United States Patent
Goodman et al.

(10) Patent No.: US 6,866,628 B2
(45) Date of Patent: Mar. 15, 2005

(54) APPARATUS FOR TEMPORARILY ENGAGING BODY TISSUE

(75) Inventors: Jack Goodman, Ann Arbor, MI (US); Tom Daigle, Corcoran, MN (US); Douglas H. Gubbin, Brooklyn Park, MN (US); David J. S. Kim, Maplewood, MN (US)

(73) Assignee: Medtronic, Inc., Minneapolis, MN (US)

( * ) Notice: Subject to any disclaimer, the term of this patent is extended or adjusted under 35 U.S.C. 154(b) by 73 days.

(21) Appl. No.: 10/122,971

(22) Filed: Apr. 11, 2002

(65) Prior Publication Data

US 2003/0195393 A1 Oct. 16, 2003

(51) Int. Cl.⁷ ................................................ A61B 1/00
(52) U.S. Cl. .................................................... 600/228
(58) Field of Search .......................... 600/37, 227–230, 600/201, 206

(56) References Cited

U.S. PATENT DOCUMENTS

| | | | | |
|---|---|---|---|---|
| 3,858,578 A | * | 1/1975 | Milo ........................... | 600/229 |
| 5,727,569 A | | 3/1998 | Benetti et al. ............... | 128/898 |
| 5,749,892 A | * | 5/1998 | Vierra et al. ................. | 600/204 |
| 5,836,311 A | | 11/1998 | Borst et al. .................. | 128/897 |
| 5,876,332 A | | 3/1999 | Looney ........................ | 600/227 |
| 6,007,486 A | | 12/1999 | Hunt et al. .................. | 600/205 |
| 6,013,027 A | * | 1/2000 | Khan et al. .................. | 600/201 |
| 6,019,772 A | | 2/2000 | Shefaram et al. ........... | 606/159 |
| 6,036,641 A | | 3/2000 | Taylor et al. ................ | 600/231 |
| 6,113,534 A | | 9/2000 | Koros et al. ................. | 600/213 |
| 6,338,712 B2 | * | 1/2002 | Spence et al. .............. | 600/201 |
| 6,464,629 B1 | | 10/2002 | Boone et al. ................. | 600/37 |
| 2003/0009080 A1 | * | 1/2003 | Peng et al. .................... | 600/37 |

FOREIGN PATENT DOCUMENTS

WO    WO 01/17437    3/2001

* cited by examiner

Primary Examiner—Kevin Shaver
Assistant Examiner—Michael B. Priddy
(74) Attorney, Agent, or Firm—Thomas G. Berry; Jeffrey J. Hohenshell

(57) ABSTRACT

An improved tissue engagement device such as a suction stabilizer or retractor. The stabilizer or retractor is provided with one or more suction pods mounted to the distal end of a flexible arm. The flexible arm is coupled to a base assembly, which attaches the arm to an associated retractor or other structure that is fixedly located relative to the operative site. The base assembly includes a fixed portion, which is coupled to the retractor or other fixed mounting point and a rotatable turret, allowing rotation of the arm relative to the fixed portion of the base assembly. A tensioning mechanism mounted to the turret applies tension to compress the turret around a corresponding pivot mounted to the fixed portion of the base to rotationally lock the turret and to lock the arm in its current configuration.

28 Claims, 9 Drawing Sheets

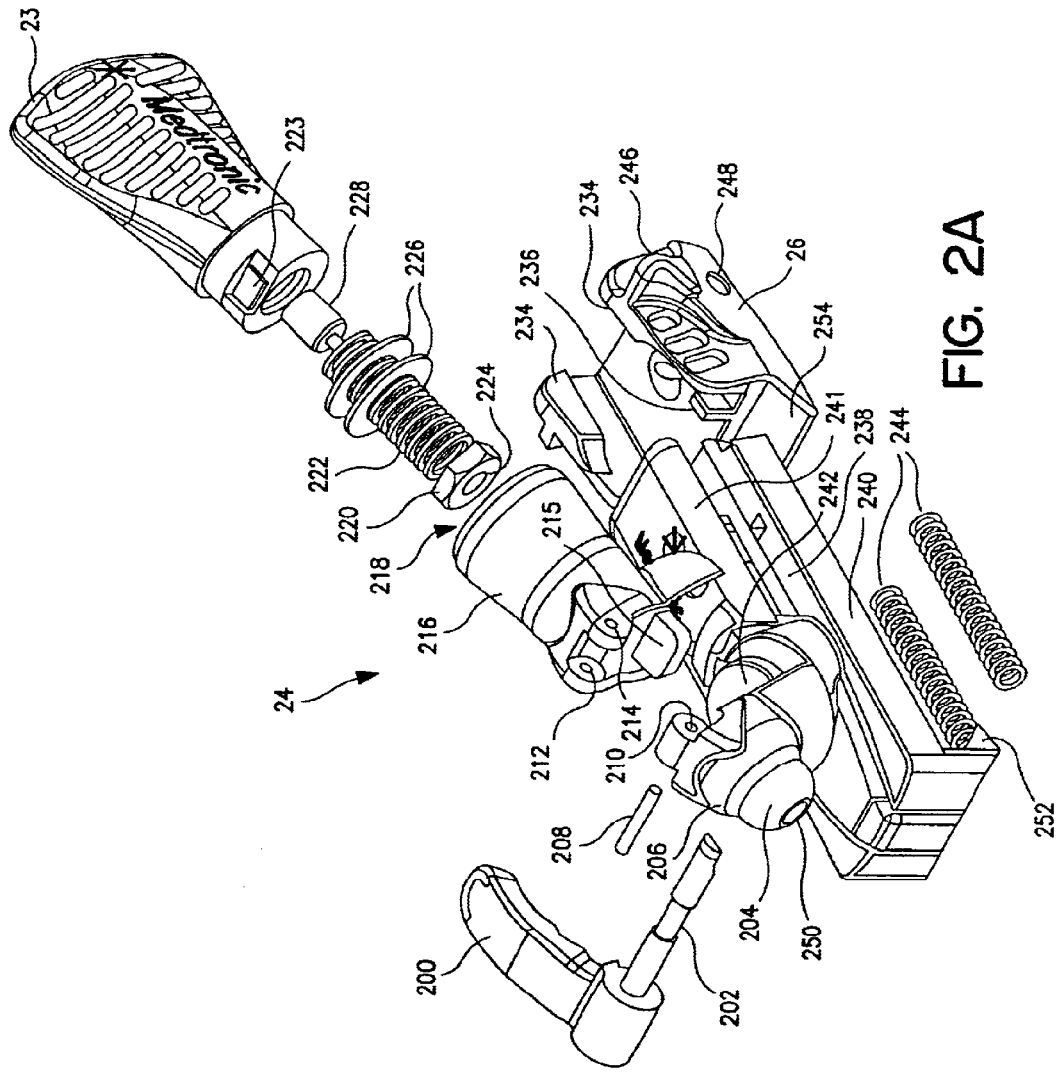

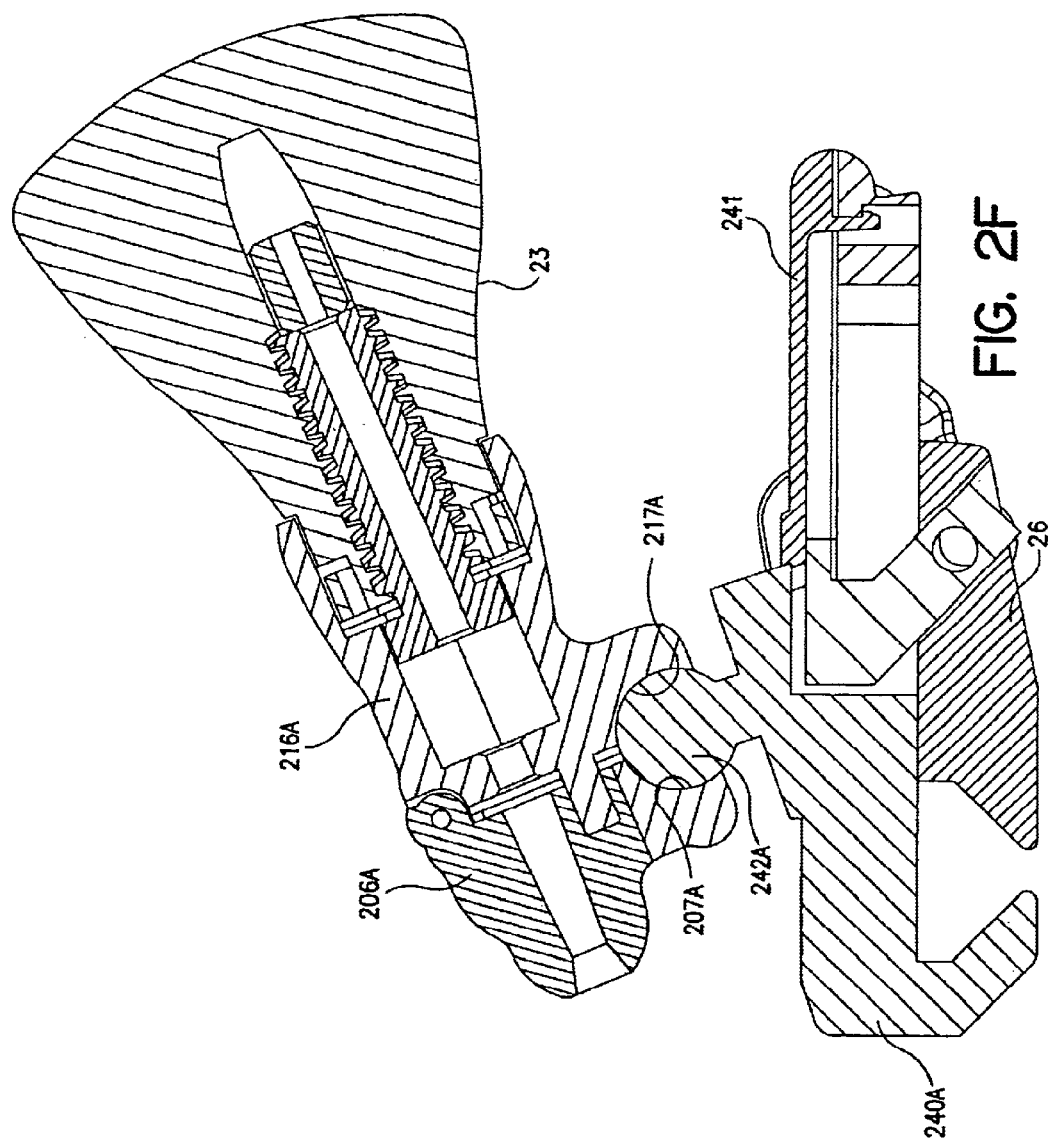

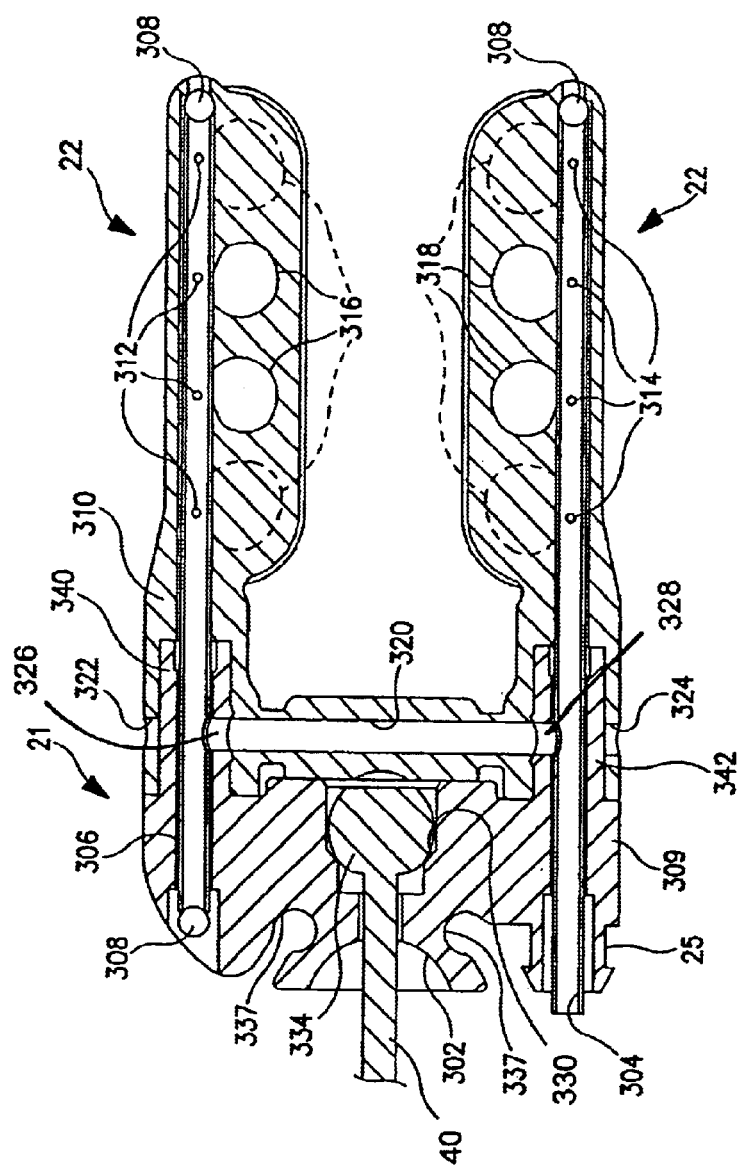
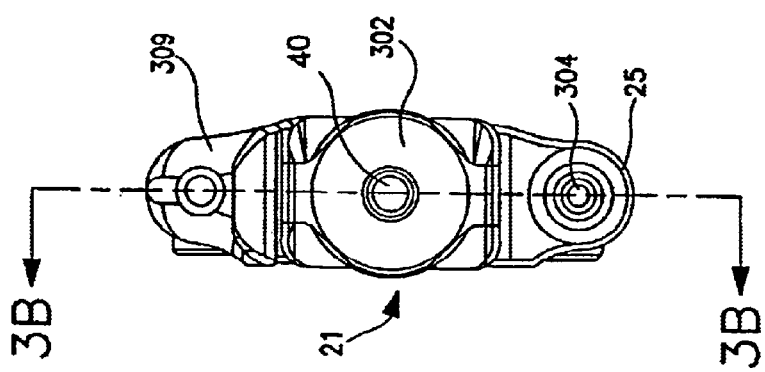
FIG. 3B
FIG. 3A

APPARATUS FOR TEMPORARILY ENGAGING BODY TISSUE

FIELD OF THE INVENTION

The present invention generally relates to surgery on body tissues and organs. More specifically, the present invention relates to methods and devices for engaging an organ, e.g. for positioning an organ in a desired orientation or for temporarily immobilizing a local area of tissue subject to motion, such as the heart wall, which permits a surgical procedure to be performed on that local area of tissue.

BACKGROUND OF THE INVENTION

Coronary artery disease remains the leading cause of morbidity and mortality in Western societies. A number of approaches have been developed for treating coronary artery disease. In less severe cases, it is often sufficient to merely treat the symptoms with pharmaceuticals or to treat the underlying causes of the disease with lifestyle modification. In more severe cases, the coronary blockage can be treated endovascularly using techniques such as balloon angioplasty, atherectomy, laser ablation, stents, and the like. In cases where these approaches have failed or are likely to fail, it is often necessary to perform a coronary artery bypass graft procedure.

The coronary artery bypass graft procedure traditionally required a heart-lung or cardiopulmonary bypass. Due to the risks incurred during cardiopulmonary bypass, beating heart bypass surgery techniques have been developed to allow coronary artery bypass without cardiopulmonary bypass. Several systems are presently available which attempt to immobilize epicardial tissue in the immediate vicinity of an anastomosis site through a pressure stabilizer employing a simple mechanical fork. Such a device stabilizes the heart by pressing a fork downwards onto the heart surface. The fork is typically mounted to an elongated arm, which in turn is typically mounted to a retractor, holding the patient's ribs apart to create an operative window. Angular movement of the arm relative to the retractor in some cases is accomplished by means of a turret, which may be clamped in its desired rotational position. Longitudinal movement of the arm relative to the retractor is typically allowed as well, and clamping mechanisms are typically provided to allow clamping of the arm to the turret and locking of the fork relative to the arm. Exemplary pressure stabilization devices are disclosed in U.S. Pat. No. 6,876,332, issued to Looney and U.S. Pat. No. 6,036,641, issued to Taylor, et al., both incorporated herein by reference in their entireties.

Suction stabilization systems, such as the Medtronic Octopus® Tissue Stabilizer (available from Medtronic, Inc., Minneapolis, Minn. USA), instead employ a comparatively long, flexible, articulating arm carrying a pair of suction paddles or pods at its distal end. During use, the arm is typically secured to a retractor, holding the patient's ribs apart to create an operative window. The pods are placed on either side of the anastomosis site and suction is applied to grip and immobilize the surface of the heart. Thereafter, tension is applied along the length of the arm to lock the arm in its position and to lock the position of the pods relative to the Arm. In Medtronic's device, is generally disclosed in pending U.S. patent application Ser. No. 09/396,047, filed by Boone, et al. on Sep. 15, 1999, for a "Method And Apparatus For Temporarily Immobilizing A Local Area Of Tissue", incorporated herein by reference in its entirety. In this device, a single knob, mounted to the proximal end of the arm, is employed to lock the arm in position and additionally to spread the pods somewhat, slightly stretching the heart's surface to provide additional stabilization of the heart surface. In such devices, all adjustment of the arm relative to the retractor is accomplished by varying the configuration of the flexible arm, prior to locking it in its desired position. Other examples of suction stabilization devices are disclosed in U.S. Pat. No. 6,113,534, issued to Koros, et al., U.S. Pat. No. 6,007,486, issued to Hunt, et al, U.S. Pat. No. 5,836,311, issued to Borst, et al. and U.S. Pat. No. 5,727,569, issued to Benetti, et al., all incorporated herein by reference in their entireties.

In conjunction with stabilization devices, suction retractors are often employed to position the heart to allow access to the desired anastomosis site. The Medtronic Starfish™ device and the Guidant Axius™ Expose™ device are examples of commercially available suction retractors. These devices employ a single, larger suction pod to engage the heart, typically in the vicinity of the heart apex. The suction pod is carried by a flexible arm, which, like the suction stabilizers discussed above, also may be locked into a desired configuration by tension applied along their length. The application of tension to the arm may also serve to lock a carrier for the suction pod relative to the arm to fix the suction pod in a desired orientation relative to the arm, as in the Guidant device. The Medtronic device is described in pending U.S. patent application Ser. No. 09/679,294, filed Jun. 12, 2001 by Keogh, et al. for a "Method and System for Organ Positioning and Stabilization, incorporated herein by reference in its entirety. The Guidant device is described in the brochure "Axius™ Expose™ Device, Instructions for Use, Guidant Corp., 2001, P/N 30462, Rev. A, also incorporated herein by reference in its entirety. Other suction retractors are described in U.S. Pat. No. 6,019,772, issued to Spence, et al. and PCT Publication No. WO 01/17437 by Peng, both also incorporated herein by reference in their entireties.

SUMMARY OF THE INVENTION

The present invention provides an improved tissue engagement device such as a suction stabilizer or retractor, which includes features intended to allow for easier use of the device and to simplify the operations necessary to lock the device in a desired configuration. In a preferred embodiment, the invention takes the form of a suction stabilizer having suction pods mounted to the distal end of a flexible arm. In this embodiment, the flexible arm is coupled to a base assembly, which attaches the arm to an associated retractor or other structure that is fixedly located relative to the operative site. The base assembly includes a fixed portion, which is coupled to the retractor or other fixed mounting point and a rotatable portion, for example, comprising a turret, allowing rotation of the arm and turret relative to the fixed portion of the base assembly. In the embodiment disclosed, the flexible arm is locked into a desired position by means of a tensioning mechanism, also mounted to the turret. The invention may also be embodied as a suction retractor, having a similar flexible arm, wherein the tensioning mechanism similarly locks the turret and the arm.

In the preferred embodiment of the present invention described in detail herein, the tensioning mechanism mounted to the turret applies tension to a cable extending through the flexible arm, to the distal end of the arm, which carries a spreading/tightening mechanism along with two suction pods. The tensioning mechanism applies tension along the entire length of the arm to compress the turret around a corresponding pivot, mounted to the fixed portion of the base, to lock the arm in its current configuration, to lock the relative location of the spreading/tightening mechanism relative to the arm and to spread the suction pods apart from one another to provide for additional stabilization at the desired anastomosis site. If the invention is embodied as a suction retractor, the tensioning mechanism would correspondingly lock the turret and arm in the same fashion, and optionally could lock a pivotably mounted carrier for the single enlarged suction pod so that the suction pod is held in its desired orientation relative to the arm.

In preferred embodiments of the invention, all operations of the tensioning mechanism are controlled by rotation of a single knob or other control mechanism, simplifying use of the device. In the disclosed embodiment of the invention, the suction pods are interconnected by means of a conduit located distal to the spreading/tightening mechanism, allowing for the use of a single vacuum line to provide vacuum to suction pods while retaining an over-all low profile to the spreading/tightening mechanism. In the disclosed embodiment of the invention, an improved clamping mechanism is also provided for locking the fixed portion of the base assembly to an associated retractor. The improved clamping mechanism employs a cam pin which is used both to move a sliding lock component upward to clamp it against the fixed portion of the base and to move the sliding lock component laterally to tighten the sliding lock component against the retractor or other fixed mounting point for the assembly.

While the various aspects of the invention are most preferably embodied in a suction stabilizer or retractor with an articulating arm, certain aspects of the invention may be useful in the context of a pressure stabilizer and/or a stabilizer with a rigid arm and/or a suction retractor with a rigid arm. In addition, it is anticipated that the invention will be applicable to similar surgical devises intended for use in other medical procedures, as they may be developed.

BRIEF DESCRIPTION OF THE DRAWINGS

The foregoing and other aspects of the present invention will best be appreciated with reference to the detailed description of a preferred embodiment of the invention in conjunction with the accompanying drawings, wherein:

FIG. 2A is an exploded view of the base assembly 24 of the embodiment illustrated in FIG. 1A.

FIG. 2F is a cross-section through an alternative embodiment to the base assembly illustrated in FIG. 2C.

FIG. 3A is a plan view of the proximal end of the tightening/spreading mechanism of the embodiment illustrated in FIG. 1A.

FIG. 3B is a sectional view through the tightening/ spreading assembly of FIG. 3A, illustrating the spreading mechanism and the construction of the suction pods.

DETAILED DESCRIPTION OF THE PRESENT INVENTION

Figure 1A:
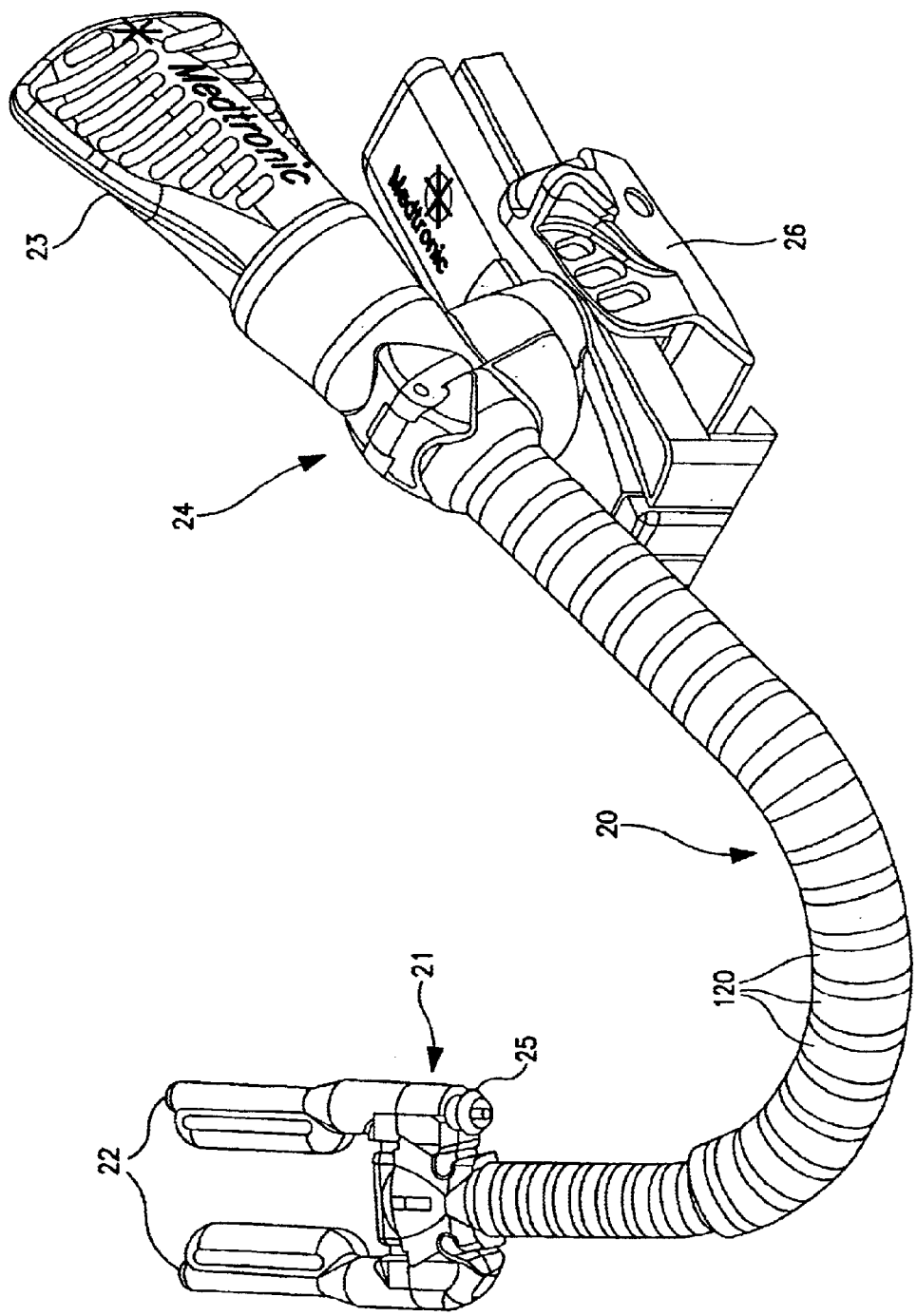
FIG. 1A is a perspective view of a suction stabilizer embodying the present invention.

FIG. 1A is a perspective view of a preferred embodiment of the invention. A flexible, articulating arm 20 is attached to base assembly 24 on the proximal end of the arm, and terminates with tightening/spreading mechanism 21 at the distal end of the arm. On the opposite, more proximal, end of base assembly 24 is handle 23, which operates to lock the arm in position, as discussed in more detail below. Extending distally beyond tightening/spreading mechanism 21 is a plurality (as shown, two) of suction paddles or pods 22. The suction pods 22 can be connected to a vacuum line by a conventional vacuum line connection 25. Each pod and its suction ports may be constructed in any acceptable manner, such as that used in the Medtronic Octopus™ tissue stabilizer. Clamp 26 is designed to attach the entire device to conventional surgical retractors or other equipment located in a fixed relation to the operative site.

Figure 1B:
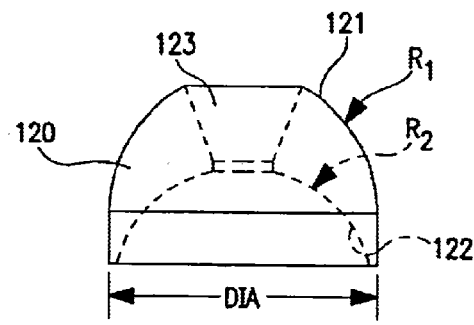
FIG. 1B illustrates a component of the flexible arm of the stabilizer of FIG. 1A.
Figure 1C:
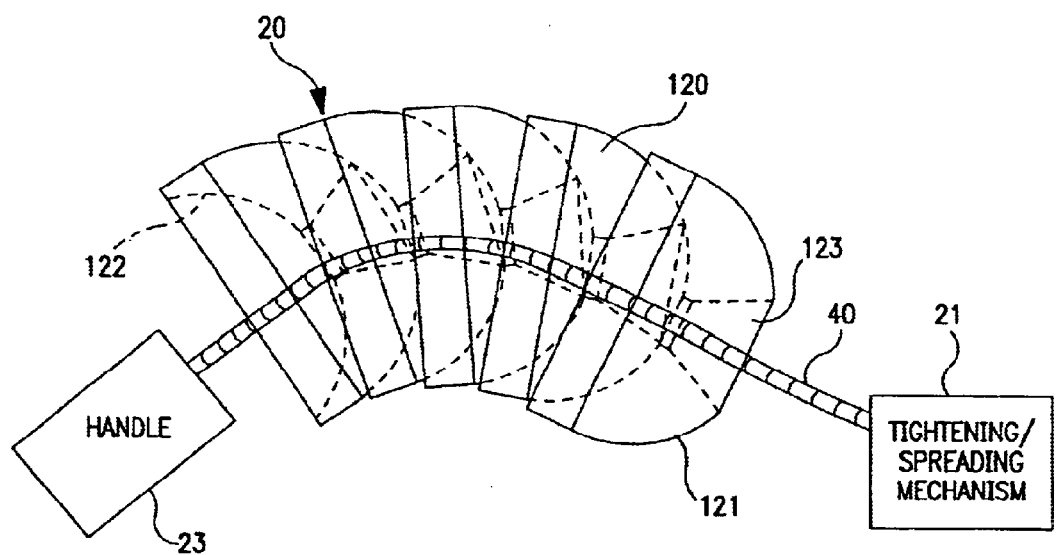
FIG. 1C illustrates the mechanism of operation of the flexible arm of the stabilizer of FIG. 1A.

The preferred embodiment shown in FIG. 1A is illustrative but not intended to be limiting insofar as the scope of the invention is concerned. For example, the handle 23 is shown in a preferred and highly stylized embodiment, but any device that performs the functions of the handle as described below would suffice. Articulating arm 20 comprises a plurality of "ball and socket" links 120, as illustrated in FIGS. 1B and 1C, discussed below. In some embodiments, the links of articulating arm 20 are covered with a thin walled elastomeric sheath, as disclosed in the above cited '047 application. The sheath serves to prevent fragile sutures from catching on the edges where the links join. The sheath is preferably manufactured of silicone rubber, although other materials, such as latex rubber or polyurethane or even collagen, may also be used.

FIG. 1B is a cross sectional view of a link used in the arm of the present invention. As seen, each link 120 has a hole 123 that passes through its center. Each link 120 comprises, on its distal end, a spherical protrusion 121; and on its proximal end, a spherical indentation 122. The spherical shapes of adjacent links are nearly identical, such that the links rotate smoothly against one another provided they are not under undue tension with each other.

Turning now to FIG. 1C, which is a partial view of a section of the links and cable showing the engagement of the cable with the sidewall of the links as the arm is bent. A cable 40 passes through hole of all of the links and is connected between the handle 23 and the tightening/ spreading mechanism 21. Rotation of handle 23 tightens the cable and causes the links to hold against each other in place. Immobilization of the links relative to each other during tightening of the cable is facilitated by the shape of the hole 123. As seen, hole is flared, having a larger opening with the surface of the spherical protrusion 121 and a smaller opening through the surface of the spherical indentation 122. The links, as seen in FIG. 1A, may vary in size along the length of the arm, with the links in the most proximal portion of the arm being largest, and the links in the most distal portion being the smallest. In the preferred embodiment, the links are fabricated out of a highly rigid engineered thermoplastic or of a metal such as stainless steel. The cable is preferably a multi-stranded stainless steel cable, having between approximately 7 to 19 strands. The links and cable may also be manufactured from other materials, including any other suitable metals or highly engineered polymers including any number of available liquid crystal polymers for the links, as well as many other types of cables, including bundle stranded, braided or cabled titanium as well as Kevlar™ for the cable. Some embodiments may also employs a textured surface molded or otherwise formed into the spherical features of the links. When the links are pulled together during tightening, the texturing causes an increase in coefficient of friction between the adjacent spherical surfaces. This has the highly desirable benefit of increasing overall system stiffness. Examples of such surfaces are also disclosed in the above cited '047 application.

FIG. 2A is an exploded drawing illustrating the various functional components of the base assembly 24 of the suction stabilizer illustrated in FIG. 1A. The base assembly 24 includes a fixed portion to be mounted to a surgical retractor or other structure having a fixed location relative to the patient and a rotatable portion or turret, rotatable relative to the fixed portion of the base. The fixed portion of the base assembly includes pivot mount 240, cover 241, lever 200 and associated cam rod 202, springs 244 and a cam pin, not shown in this view. The rotatable portion of the base assembly includes the turret, comprising first and second turret halves 206 and 216 and hinge pin 208, and the tensioning mechanism comprising handle 23, threaded shaft 222, washers 226 and sleeve 228 which, as assembled, is mounted to the proximal end of the tension cable 40 (FIG. 1C). A spherical projection 204 is formed on the distal end of turret half 206, which is inserted in the corresponding spherical recess of the first link 120 (FIG. 1A) of the flexible arm.

Pivot mount 240 carries the turret pivot 242, which takes the form of a disk topping a cylindrical section extending upward and at an angle from the pivot mount 240. First and second turret halves 206 and 216, when assembled, are mounted around the turret pivot 242, allowing the turret and attached flexible arm to pivot relative to the fixed portion of the base assembly. The first and second turret halves 206 and 216 are provided with grooved portions 207, 217, adapted to engage with the disk-shaped top portion of turret pivot 242, allowing rotation but preventing removal of the first and second turret members 206 and 216. Turret halves 206 and 216 are connected to one another by means of hinge pin 208. When assembled, hinge pin 208 passes through bore 212 in the second turret half 216, through bore 210 in the first turret half 206 and then is anchored in bore 214 of the second turret half 216. By this arrangement, turret halves 206 and 216 may pivot relative to one another. The dimensions of the internally formed grooves in turret halves 206 and 216 are such that when the two components are pivoted around pin 208 such that their lower extremities are in close proximity to one another, they correspondingly clamp inwardly around the turret pivot 242, locking the turret rotationally into position relative to the fixed portion of the base assembly. When assembled, projection 215 is located in a corresponding recess in turret half 206, maintaining the turret halves in alignment.

The mechanism for tensioning cable 40 (FIG. 1C) is carried by the turret and includes handle 23, threaded shaft 222, washers 226 and sleeve 228. When assembled, sleeve 228 is tightly crimped to the end of the tension cable 40 which, in the device as assembled, extends through the internal bore 224 of threaded member 222, through first and second turret halves 206 and 216 and out the opening 250 on the distal surface 204 of the first turret component 206. Like the device described in the above cited '047 application, rotation of handle 23 causes tension to be applied to the cable 40, tightening the elements of the flexible arm relative to one another to a fixed position. Concurrently, tightening of the cable also causes first and second turret halves 206 and 216 to pivot toward one another, causing them to clamp circumferentially around turret pivot 242.

Operation of the tensioning mechanism is as follows. The distal extremity of the threaded member 220 is provided with a hexagonally shaped distal portion 220, which is located in a corresponding hexagonally configured recess 218 in the proximal portion of the second turret half 216. Threaded member 222 is free to slide within this recess, but cannot rotate. When assembled, washers 226 are located within the proximal end of the first turret half 216, and provide a bearing surface against which handle 23 rotates. Handle 23 is provided with internal threading corresponding to the external threading on member 222. Rotation of handle 23 thus causes proximal movement of member 222 against sleeve 228, in turn causing proximal movement of the cable 40, correspondingly tightening the components of the articulating arm and the turret, to affix them in their desired positions. Resilient tabs 223 of handle 23 cooperate with corresponding notches formed in the second turret half 216 to prevent over-rotation of the handle 23 and consequent detachment of the handle. This aspect of the operation of the tensioning mechanism is discussed in more detail below in conjunction with FIG. 2E.

As discussed below, proximal movement of cable 40 also serves to stabilize the location of the spreading mechanism 21 at the distal portion of the arm (as illustrated in FIG. 1A) as well as causing the suction pods 22 (also illustrated in FIG. 1A) to move outward relative to one another. Thus, in the invention that as disclosed, rotation of the knob 23 accomplishes four functions as a result of tensioning the cable, including clamping of the turret to the fixed portion of the base, locking the flexible arm in its then present configuration, locking the position of the tightening/spreading mechanism 21 and pods 20 relative to the distal end of the flexible arm, and shortly thereafter or concurrently, spreading the suction pods 220 apart from one another to stretch the heart tissue located between the pods. The structural relationship of the various components of FIG. 2A is illustrated in more detail in FIG. 2C, discussed below.

Mounted to the fixed portion of the base assembly is sliding clamp 26. Clamp 26 is provided with inwardly directed tabs 234 and is also provided with two upwardly extending projections 236. When assembled, projections 236 are located adjacent the distal ends of springs 244, which lie in downwardly extending grooves formed in the lower surface of pivot mount 240 and urge clamp 26 distally. Handle 200 and cam rod 202 also make up a portion of the clamping mechanism, passing through bore 248 in the clamp 26. Functional operation of the clamp 232 is described in more detail in conjunction with FIGS. 2C and 2D, discussed below.

Figure 2B:
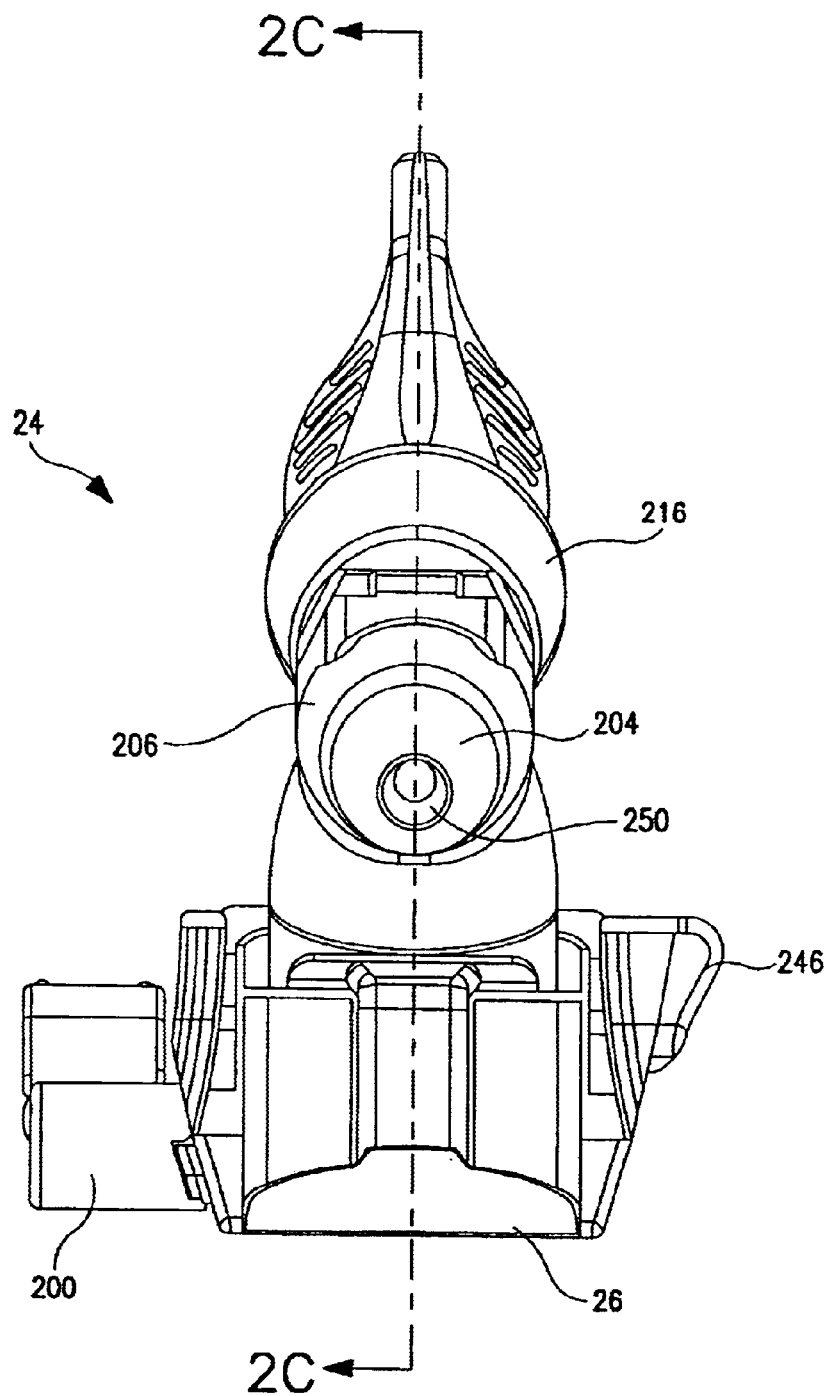
FIG. 2B is a perspective view of the distal end of the base assembly 24, illustrated in FIG. 1A.

FIG. 2B is a plan view of the distal surface of the base assembly 24 after assembly. All numbered components illustrated correspond to identically numbered components in FIG. 2A. In this view, it can be seen that the first and second turret halves 206 and 216, respectively, are mounted closely adjacent to one another and around the turret pivot 242 (not visible in this view). FIG. 2B also illustrates the line along which the cross-section of FIG. 2C is taken.

Figure 2C:
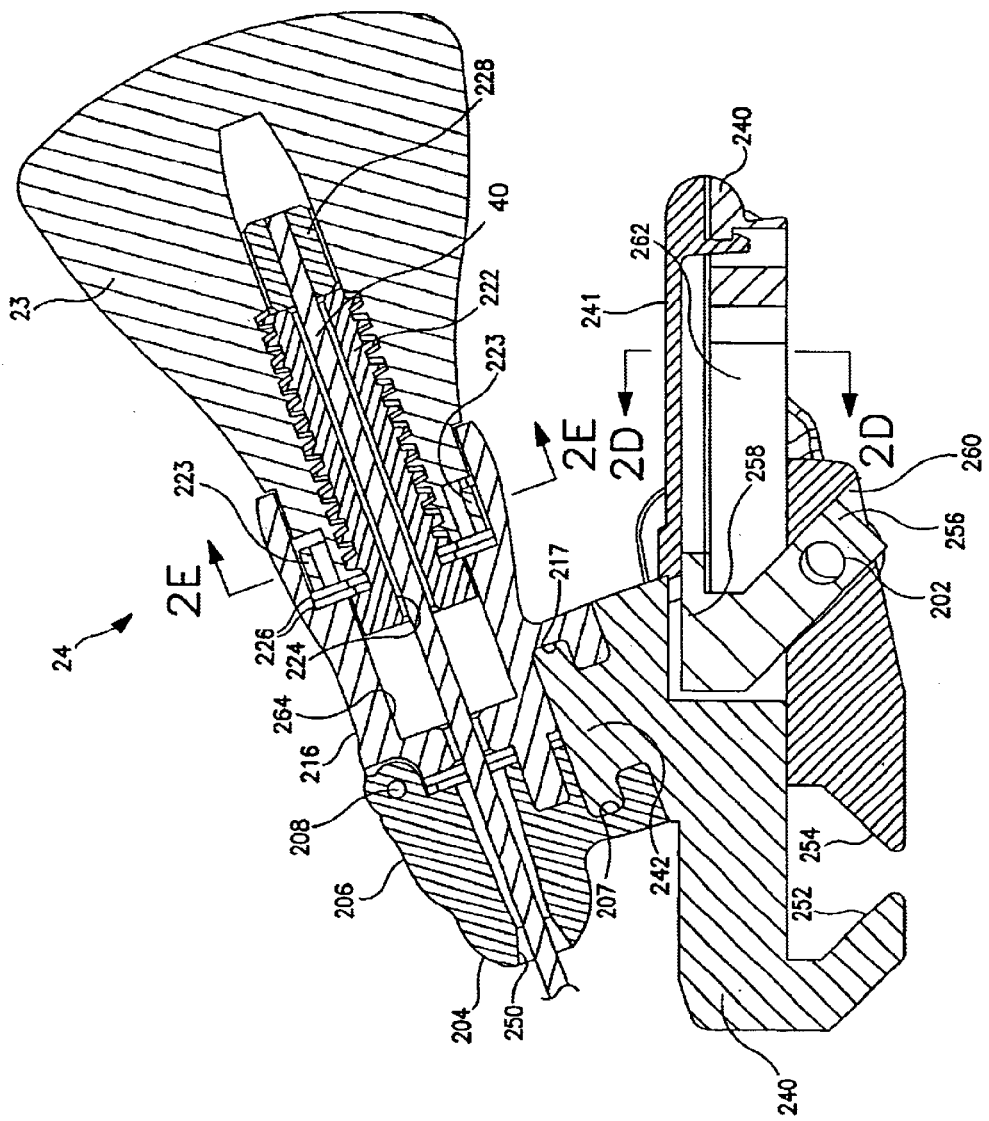
FIG. 2C is a cross-sectional view through the base assembly illustrated in FIGS. 2A and 2B.

FIG. 2C is a sectional view through the base assembly 24 illustrated in FIGS. 2A and 2B. In this view, the functional inter-relationship of the components of the base assembly can better be appreciated. All components correspond to identically numbered components in FIGS. 2A and 2B.

In this view, turret halves 206 and 216 are shown mounted to one another by means of hinge pin 208, and the inter-relation of the internal circumferential grooves 207, 217 in turret halves 206 and 216 can be appreciated. These grooves are shown as located closely adjacent to the outer surface of the pivot 242. Movement of the lower portions of the turret halves 206 and 216 toward one another due to tension provided by the cable 40 tightly clamps the turret to the turret pivot 242. Handle 23 is shown with its threaded inner surface engaging the threaded member 222 and its distal surface lying adjacent washers 226, located in a recess formed in the proximal end of turret component 216. The hexagonally shaped distal portion of threaded member 222 is shown lying within a correspondingly configured lumen 264 formed within turret half 216, allowing for longitudinal movement of threaded member 220 but not rotational movement. Sleeve 228 is shown located within the handle 23, adjacent the proximal end of threaded member 222 and is mounted to the proximal end of the tension cable 40.

More clearly visible in this view is the mechanism by which clamp 26 operates in conjunction with the pivot mount 240 to provide a mechanism for attaching the assembly to an associated chest retractor. Pivot mount 240 is provided with a downwardly extending projection having a proximally facing angled surface 252, corresponding to a distally facing angled surface 254 on the distal end of clamp 26. In use, a portion of a retractor is located between these two slanted surfaces, and clamp 26 is moved distally as far as possible so that that portion of the retractor is held between pivot mount 240 and clamp 26. Cam pin 256 is located within an angled bore 260 formed in clamp 26, having its lower extremity located proximal to its upper extremity. Pin 256 extends through and is located slidably within a downwardly extending slot 262, formed in pivot mount 240. Although not shown in this view, the enlarged head portion 258 of pin 256 bears downwardly along the upper surface 238 of the pivot mount 240. Cam rod 202 has its camming surface located within a cross bore in the pin 256, configured so that rotation of the handle 200 and associated cam rod 202 pulls the pin downward relative to the pivot mount 240 and is correspondingly pulls clamp 26 upward into tight contact with pivot mount 240. Because pin 256 and bore 260 are angled less than 90 degrees relative to the axis along which the clamp 26 slides, rotation of the cam rod 202 by means of lever 200 (FIG. 2B) also causes a slight distal movement of clamp 26 relative to the pivot base 240, tightening it against the associated retractor as well. Cover 241 is shown mounted to the pivot mount 240, covering the slot 262 in which the pin 256 is mounted.

Figure 2D:
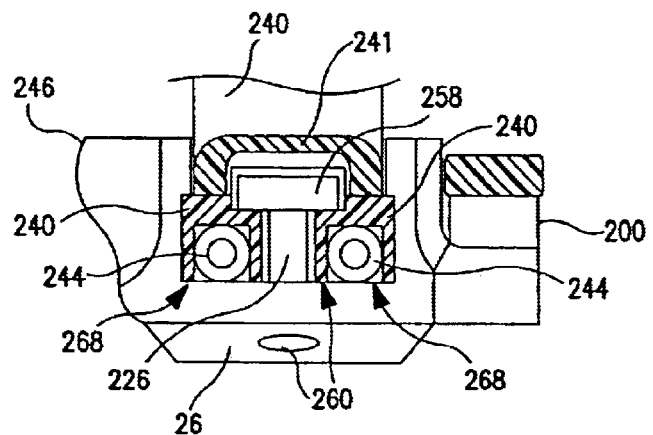
FIG. 2D is a partial cross-section through a first portion of the base assembly illustrated in FIG. 2C.

FIG. 2D is a partial cross-section through the fixed portion of the base assembly 24 illustrated in FIG. 2C. In this view, it can be seen that the pivot mount 240 is provided with two downwardly extending longitudinal grooves 268, in which springs 244 are mounted. The distal ends of these springs bear against the upwardly extending projections 236 (FIG. 2A) on clamp 26 and the proximal ends of these springs bear against projections located within grooves 268 in order to urge clamp 26 in a distal direction relative to the pivot mount 240. Also visible in this view is the configuration of cam pin 266, showing its enlarged head portion 258 riding along the upper surface 238 of the pivot mount 240. All other numbered components correspond to identically numbered components in the figures above.

Figure 2E:
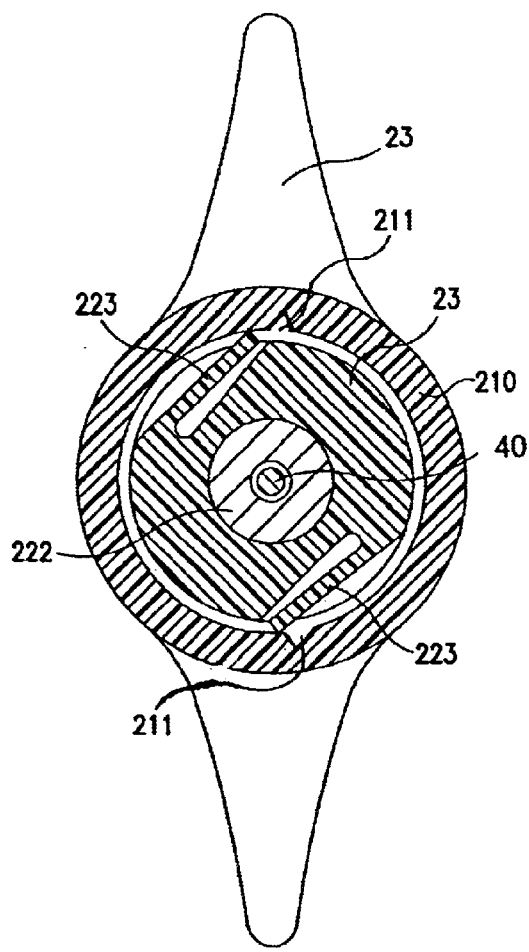
FIG. 2E is a cross-section through a second portion of the base assembly illustrated in FIG. 2C.

FIG. 2E is a partial cross-section through the proximal portion of the second turret half 216, illustrating the inter relation of the resilient tabs 223 on knob 23 and the internal lumen formed in turret half 216. As illustrated, resilient tabs 223 are compressed inward against the inner surface of the lumen in the proximal portion of turret half 216. Formed adjacent to the proximal edge of the turret half 216 are two triangular depressions 211, formed to correspond to the free ends of the resilient tabs 233. When the threaded rod 222 is bottomed within the second turret half 216, rotation of the knob in a counter clockwise direction (as viewed from the proximal end of the turret assembly) causes the knob to move proximally relative to the second turret half 216. At such time as the resilient tabs 233 move sufficiently proximally, they will latch into triangular indentations 211, preventing further rotation of knob 23. Because threaded shaft 222 is still threaded into the interior of the knob 23 at this point, the knob remains attached to the base assembly and cannot be inadvertently removed.

FIG. 2F illustrates a cross-sectional view through an alternative embodiment to the base assembly illustrated in FIG. 2C. In this view, the configuration of the majority of the components is identical to that illustrated in FIG. 2C, with the following exceptions. Pivot mount 240A is provided with a spherical pivot 242A rather than a disk shaped pivot as in the embodiment of FIG. 2C. Correspondingly, turret halves 206A and 216A are provided with spherical recesses 207A and 217A, rather than circumferential slots as in the embodiment of FIG. 2C. This alternative embodiment provides a base assembly with a higher profile, but allows for increased adjustability of the position of the turret relative to the base, as compared to the embodiment illustrated in FIG. 2C. All other aspects of operation of the device correspond to those discussed above in conjunction with FIG. 2C.

FIG. 3A is a plan view of the proximal end of the tightening/spreading mechanism 21 of the suction stabilizer illustrated in FIG. 1A. The tension cable 40 is visible in cross-section, exiting through bore in the proximal surface of the tightening/spreading mechanism 21. A spherical recess 302 is formed in the proximal surface of tightening/spreading mechanism 21, which receives the corresponding spherical surface of the last link 120 (FIG. 1A) of the flexible arm. Located concentrically within the vacuum connector 25 is a metallic tube 304, which functions to deliver vacuum to the suction pods 22, mounted to the spreading/tightening mechanism 21. FIG. 3A also illustrates the cross-sectional line along which the view of FIG. 3B is taken.

FIG. 3B shows the spreading/tightening mechanism 21 of FIG. 1, in conjunction with the vacuum pods 22. In this view it can be seen that the spreading/tightening mechanism 21 includes a first molded plastic component 309. A metal ball 332, located at the distal end of cable 230 is located within a corresponding generally cylindrical recess 335 formed in plastic component 309. Ball 334 may be provided with a silicone coating to reduce friction. A portion of the recess 332 is formed as an angled surface 330, which also engages a portion of the proximal surface of ball 334. In operation, the proximal movement of cable 230 caused by rotation of handle 23, as discussed above, causes the proximal surface of ball 334 to bear against the angled surface 330, causing deformation of member 309 and corresponding spreading of the suction pods 22, relative to one another. Indentations 337, molded into component 309 serve to define hinge points.

Suction pods 22 correspond generally to those described in conjunction with the '047 application, cited above. However, rather than delivering vacuum individually to each pod, only a single vacuum line is required, coupled to vacuum connector 25. Distribution of vacuum to both pods is accomplished by means of a cross bore 320, molded into the plastic component 310 which forms the body of suction pods 22.

Malleable metal tubes 304 and 306 are shown located within longitudinally aligned bores within components 309 and 310. Tube 304 extends to the vacuum connector 25, and serves as the vacuum source for both pods 22. The proximal end of tube 306 is capped by ball 308, and the recess adjacent to it is backfilled, for example with silicone rubber. The distal ends of both tubes 304 and 306 are similarly capped with balls 308 and backfilled. Cross bore 320 extends all the way through the molded plastic component 309. However, it is sealed at its ends by means of the tubular projections 340 and 342 of component 309. After assembly, the slight recesses 322 and 324 may be filled with silicone rubber. Malleable tubes 304 and 306 are formed such that each is provided with a laterally directed opening 328, 326 which as assembled aligns with the cross bore 320, providing a mechanism for communicating vacuum applied to tube 304 to tube 306, and thereby evenly applied to both suction pods 22. Vacuum applied to tube 304 is delivered to cup shaped recesses in each of the pods, indicated at 316 and 318, by means of bores 312 and 314, in a fashion similar to that as employed in the presently available Medtronic devices.

Figure 3C:
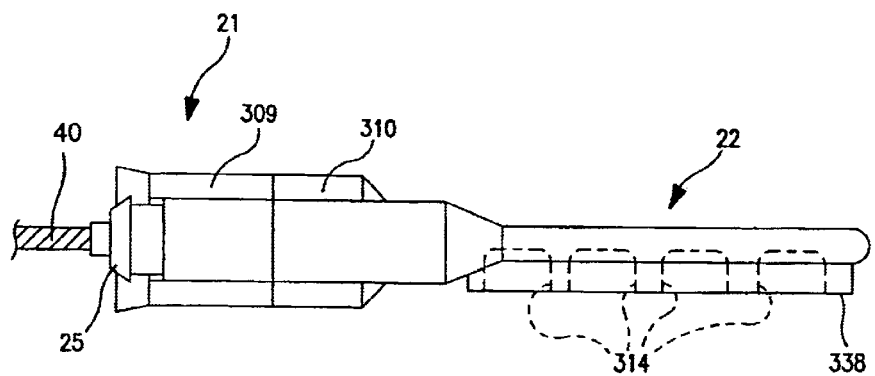
FIG. 3C is a side plan view of the tightening/spreading mechanism and suction pods of FIGS. 3A and 3B.

FIG. 3C is a side plan view of the spreading/tightening mechanism 21 and suction pods 22 illustrated in FIG. 3B. Numbered components correspond to identically numbered components in FIG. 3B. In this view, the general configuration of the pods 22 and of the cup shaped recesses 314, illustrated in broken outline, can be seen. The lower surface of the pods is molded to define a generally arcuate surface 338 for improving adhesion of the pods to the heart surface.

In the embodiments illustrated above, the stabilizer is disclosed as a stabilizer having a flexible, articulating arm. As noted above, the invention may similarly be practiced in a suction retractor with an articulating arm. Moreover, certain aspects of the invention might also be used fully practiced in the context of a stabilizer or retractor with a rigid arm. For example, the ability to simultaneously rotationally lock the turret relative to the fixed portion of the base assembly in conjunction with adjustment of the angular position of the spreading/tightening assembly relative to the arm or adjustment of the position of the suction pod of a retractor relative to the arm would still be desirable. Similarly, in the context of a suction stabilizer with a rigid arm, the ability to simultaneously lock the turret rotationally relative to the fixed portion of the base and spread the pods 22 would still be valuable. The various features discussed above in conjunction with the lock, the spreading/tightening mechanism could also usefully be employed in a stabilizer with a rigid arm. Similarly, while the disclosed embodiments of the invention take the form of a suction stabilizer, inclusion of the ability to simultaneously adjust the position of the turret relative to the fixed portion of the base and adjust the position of the tissue contact members in a pressure stabilization device would also be of use in a pressure stabilizer.

While the disclosed embodiment employs a knob and a threaded shaft to apply tension to the cable, causing the locking of the turret to the fixed portion of the base assembly, alternative mechanisms for applying tension to the cable could of course be substituted. For example, the tensioning mechanisms disclosed in U.S. Pat. No. 6,007,486 issued to Hunt, et al., U.S. Pat. No. 5,899,425 issued to Corey, et al. and U.S. Pat. No. 6,264,605 issued to Sirica, et al. could all usefully be substituted for the tensioning mechanism of the present invention, while remaining within the scope of the present invention. As such, the above description and associated drawings should be considered as exemplary, rather than limiting, with regard to the scope of the claims which follow:

In conjunction with the above specification, we claim:

1. A tissue engaging device, comprising:
   an elongated arm, the arm being flexible to display multiple configurations, having a proximal end and a distal end and a longitudinal axis;
   a tissue engagement mechanism, mounted to the distal end of the arm;
   a base assembly comprising a fixed base member having a pivot and a rotatable base member mounted on the pivot; the proximal end of the arm on the rotatable base member to provide rotation of the axis of the arm at its proximal end relative to the fixed base member;
   a tension member extending through the rotatable base member and arm; and
   a tensioning mechanism mounted to the base assembly, the tensioning mechanism operably coupled to apply tension to the tension member to concurrently compresses the rotatable member around the pivot to rotationally lock the rotatable base member to the fixed base member and lock the flexible arm in its then current configuration.

2. A device as in claim 1 wherein the tissue engagement mechanism is pivotably attached to the arm.

3. A device as in claim 2 wherein the tensioning mechanism concurrently locks the tissue engagement mechanism in a pivotal position by application of tension on the tension member.

4. A tissue engaging device, comprising:
   an elongated arm having a proximal end and a distal end and a longitudinal axis;
   a tissue engagement mechanism, pivotably mounted to the distal end of the arm;
   a base assembly comprising a fixed base member comprising a pivot and a rotatable base member mounted around the pivot and attached to the proximal end of the arm, the rotatable base member rotatable to provide rotation of the axis of the arm at its proximal end relative to the fixed base member;
   a tension member extending through the rotatable base member and arm to the tissue engagement mechanism; and
   a tensioning mechanism mounted to the rotatable base member, the tensioning mechanism operably coupled to apply tension to the tension member to concurrently rotationally lock the rotatable base member to the fixed base member by compressing the rotatable base member around the pivot and lock the position of the tissue engagement mechanism relative to the arm.

5. A device as in claim 4, wherein the tissue engagement mechanism comprises a suction pod.

6. A device as in claim 5, wherein the tissue engagement mechanism comprises two suction pods.

7. A device as in claim 4 wherein the arm is flexible to conform to multiple shapes.

8. A device as in claim 7 wherein the tensioning mechanism concurrently locks the flexible arm in its current shape by application of tension on the tension member.

9. A tissue engaging device, comprising:
   an elongated arm having a proximal end and a distal end and a longitudinal axis;
   a tissue engagement mechanism mounted to the distal end of the arm, the tissue engagement mechanism comprising first and second tissue contact members extending from the distal end of the arm and means for spreading the tissue contact members apart from one another responsive to applied tension;

a base assembly comprising a fixed base member and a rotatable base member mounted to the proximal end of the arm, the rotatable base member rotatable to provide rotation of the axis of the arm at its proximal end relative to the fixed base member;

a tension member extending through the rotatable base member and arm to the tissue engagement mechanism; and a tensioning mechanism mounted to the rotatable base member, the tensioning mechanism operably coupled to apply tension to the tension member to concurrently rotationally lock the rotatable base member to the fixed base member and spread the tissue contact members apart from one another.

10. A device as in claim 9, wherein the fixed base member comprises a pivot and wherein the rotatable base member is mounted around the pivot and wherein application of tension to the tension member compresses the rotatable member around the pivot.

11. A device as in claim 10, wherein the rotatable base member comprises two components pivotably mounted to one another and wherein application of tension to the tension member pivots the two components relative to one another to compress the components around the pivot.

12. A device as in claim 11, wherein the pivot comprises a projection from the fixed base member having a circular circumferential surface and wherein application of tension to the tension member pivots the two components relative to one another to compress the components around the circular circumferential surface of the pivot.

13. A device as in claim 12, wherein the circular circumferential surface of the pivot is a cylindrical surface.

14. A device as in claim 12, wherein the circular circumferential surface of the pivot is a spherical surface.

15. A device as in claim 9 wherein the tissue contact members are suction pods.

16. A device as in claim 9 wherein the arm is flexible.

17. A device as in claim 16 wherein the tensioning mechanism concurrently locks the flexible arm in a rigid position by application of tension on the tension member.

18. A device as in claim 9 wherein the tissue engagement mechanism is pivotably attached to the arm.

19. A device as in claim 18 wherein the tensioning mechanism concurrently locks the position of the tissue engagement mechanism relative to the arm by application of tension on the tension member.

20. A device as in claim 9 wherein the rotatable base member is a turret.

21. A device as in claim 9 wherein the fixed base member is a sliding clamp.

22. A suction stabilizer comprising:

A flexible, elongated arm having a proximal end and a distal end;

a tension member extending through the arm;

a spreading mechanism mounted to the distal end of the arm and coupled to the tension member;

a tensioning mechanism mounted to the proximal end of the arm, the tensioning mechanism operably coupled to apply tension to the tension member to concurrently lock the arm in a desired configuration and spread tissue contact members apart from one another;

first and second suction pods mounted to and extending distally from the spreading mechanism, each having a tissue engaging surface and each including a suction port open to the tissue engaging surface and an internal passageway coupled to the suction port;

a conduit located distal to the spreading mechanism and open to both of the internal passageways; and a suction inlet to the conduit.

23. A stabilizer as in claim 22, further comprising a base assembly comprising a fixed base member and a rotatable base member mounted to the proximal end of the arm the rotatable base member rotatable to provide rotation of the axis of the arm at its proximal, end relative to the fixed base member.

24. A stabilizer as in claim 23, wherein the tensioning mechanism is operably coupled to apply tension to the tension member to concurrently lock the rotatable base member in a desired rotational position relative to the fixed base member.

25. A tissue engaging device, comprising:

a base assembly; and an elongated arm having a proximal end mounted to the base assembly and a distal end carrying a tissue engagement mechanism;

wherein the base assembly comprises:

a base member with an upper surface, an elongated slot open to the upper surface and a downwardly extending projection;

a lock member mounted to the base assembly and slidable along the base member along a first axis toward the downwardly extending projection, the lock member having an internal downwardly extending bore, angled less than 90 degrees relative to the first axis and a cross bore, intersecting the angled bore;

a pin with an enlarged head and a cross-bore, the pin mounted in the bore of the lock member and extending through the elongated slot in the base member, the enlarged head engaging the upper surface of the base member; and a cam rod extending through the cross bores in the lock member and pin.

26. A device as in claim 25, wherein the tissue engagement mechanism comprises a suction pod.

27. A device as in claim 18 wherein the tissue engagement mechanism comprises two suction pods.

28. A device as in claim 25 or claim 26 or claim 27, wherein the arm is a flexible arm.

* * * * *

UNITED STATES PATENT AND TRADEMARK OFFICE
CERTIFICATE OF CORRECTION

PATENT NO. : 6,866,628 B2  Page 1 of 1
APPLICATION NO. : 10/122971
DATED : March 15, 2005
INVENTOR(S) : Goodman et al.

It is certified that error appears in the above-identified patent and that said Letters Patent is hereby corrected as shown below:

Column 10, line 53, that portion of the claim reading "as in claim 4," should read --as in claim 1 or claim 4,--.

Column 12, line 19, that portion of the claim reading "arm the" should read --arm, the--.

Column 12, line 21, that portion of the claim reading "proximal, end" should read --proximal end--.

Column 12, line 53, that portion of the claim reading "in claim 18" should read --in claim 26--.

Signed and Sealed this

Tenth Day of April, 2007

JON W. DUDAS
*Director of the United States Patent and Trademark Office*